United States Patent
Takahashi et al.

(10) Patent No.: US 7,078,517 B2
(45) Date of Patent: Jul. 18, 2006

(54) METHOD OF REUSING DNA-IMMOBILIZATION SUBSTRATE

(75) Inventors: Kojiro Takahashi, Hiroshima (JP); Osamu Takai, Hiroshima (JP); Michifumi Tanga, Yamaguchi-ken (JP)

(73) Assignees: Toyo Kohan Co., LTD, Tokyo (JP); Nihon Parrkerizing Hiroshima Co., LTD, Hiroshima (JP); Tojiro Takahashi, Hiroshima (JP)

( * ) Notice: Subject to any disclaimer, the term of this patent is extended or adjusted under 35 U.S.C. 154(b) by 265 days.

(21) Appl. No.: 10/451,399

(22) PCT Filed: Dec. 17, 2001

(86) PCT No.: PCT/JP01/11027
§ 371 (c)(1),
(2), (4) Date: Dec. 9, 2003

(87) PCT Pub. No.: WO02/054068
PCT Pub. Date: Jul. 11, 2002

(65) Prior Publication Data
US 2004/0092005 A1    May 13, 2004

(30) Foreign Application Priority Data
Dec. 28, 2000    (JP)    .............................. 2000-401624

(51) Int. Cl.
*C07H 23/00*    (2006.01)

(52) U.S. Cl. .............................. 536/26.43; 536/26.42; 536/25.41; 536/25.4; 536/23.1

(58) Field of Classification Search .................... 435/6, 435/5, 4; 536/26.43, 26.42, 25.41, 25.4, 536/23.1
See application file for complete search history.

(56) References Cited

U.S. PATENT DOCUMENTS 6,043,353 A * 3/2000 Pon et al. .................. 536/25.3
2004/0209269 A1 * 10/2004 Dugas et al. .................. 435/6

FOREIGN PATENT DOCUMENTS

WO    WO 97/23496    7/1997

* cited by examiner

*Primary Examiner*—T. D. Wessendorf
(74) *Attorney, Agent, or Firm*—Browdy and Neimark, PLLC

(57) ABSTRACT

It is intended to provide a method of reusing a DNA-immobilization substrate whereby the expensive DNA-immobilization substrate can be efficiently utilized and a reusable DNA-immobilization substrate having the same performance as a new product without any trouble in practical use can be provided. Namely, a method of reusing a DNA-immobilization substrate characterized in that, to remove DNA from a DNA-immobilization substrate carrying the DNA immobilized by an acid-amide bond via an oligonucleotide to thereby enable the immobilization of a fresh DNA, the acid-amide bond between the substrate and the DNA is hydrolyzed with an acid or an alkali.

2 Claims, 1 Drawing Sheet though it is widely noticed in the field of biochemical, molecular biological and gene engineering studies or medical examinations, as making it possible to treat a large number minor samples and to analyze the reaction data through spectroscopy in a rapid and simplified manner.
METHOD OF REUSING DNA-IMMOBILIZATION SUBSTRATE

TECHNICAL FIELD

The present invention relates to a method of reusing DNA-immobilization substrates.

BACKGROUND ART

Heretofore, a substrate for DNA diagnosis has been used as one means of gene analysis, etc. A DNA-immobilization substrate accepts a large number of DNA fragments and oligonucleotides aligned on the surface of its solid phase, and it is widely noticed in the field of biochemical, molecular biological and gene engineering studies or medical examinations, as making it possible to treat a large number minor samples and to analyze the reaction data through spectroscopy in a rapid and simplified manner.

Though such DNA-immobilization substrates are extremely expensive, a method of reusing the used substrates for again immobilizing any other DNA thereon has not as yet been developed. Therefore, used substrates are generally disposed of, and even though they are reused, the DNA having been previously immobilized thereon may still remain on them and most used substrates are no longer practicable.

The present invention is to solve the above-mentioned problems and to provide a method of reusing once-used DNA-immobilization substrates for efficient utilization of expensive DNA-immobilization substrates, in which the reused DNA-immobilization substrates have the same performance as that of new substrates with no trouble in practical use, and the invention is to reduce the economical and technical load to DNA-immobilization substrate users.

DISCLOSURE OF THE INVENTION

We, the present inventors have assiduously studied to attain the above-mentioned object and, as a result, have found out a method of completely removing DNA from a DNA-immobilized substrate that has been repeatedly used for PCR amplification and a possibility of DNA re-immobilization on the refreshed substrate.

Specifically, the invention of claim 1 provides a method of reusing a DNA-immobilization substrate, which comprises removing the immobilized DNA from a DNA-immobilization substrate having a DNA immobilized thereon through acid amido-bonding via an oligonucleotide to thereby refresh the substrate so that it can receive a new DNA to be immobilized thereon, and which is characterized in that the acid amido-bonding between the substrate-DNA is hydrolyzed with an acid or alkali.

The invention of claim 2 provides a method of reusing a DNA-immobilization substrate, which comprises processing a DNA-immobilization substrate with a DNA immobilized thereon via an acid amido-bonding to thereby hydrolyze the acid amido-bonding between the substrate-DNA with an acid, and then dipping it in an alkali to remove anions so as to convert the substrate surface into an amino group-modified surface.

The invention of claim 3 provides a method of reusing a DNA-immobilization substrate, which comprises processing a DNA-immobilization substrate with a DNA immobilized thereon via an acid amido-bonding to thereby hydrolyze the acid amido-bonding between the substrate-DNA with an alkali so as to convert the substrate surface into an amino group-modified surface.

The acid for hydrolysis in the invention is preferably one or more acids of mineral acids and organic acids, as in claim 4.

Also preferably, the alkali for hydrolysis is any of alkali metal hydroxides and/or an alkali metal salts as in claim 5.

BEST MODES FOR CARRYING OUT THE INVENTION

Figure 1:
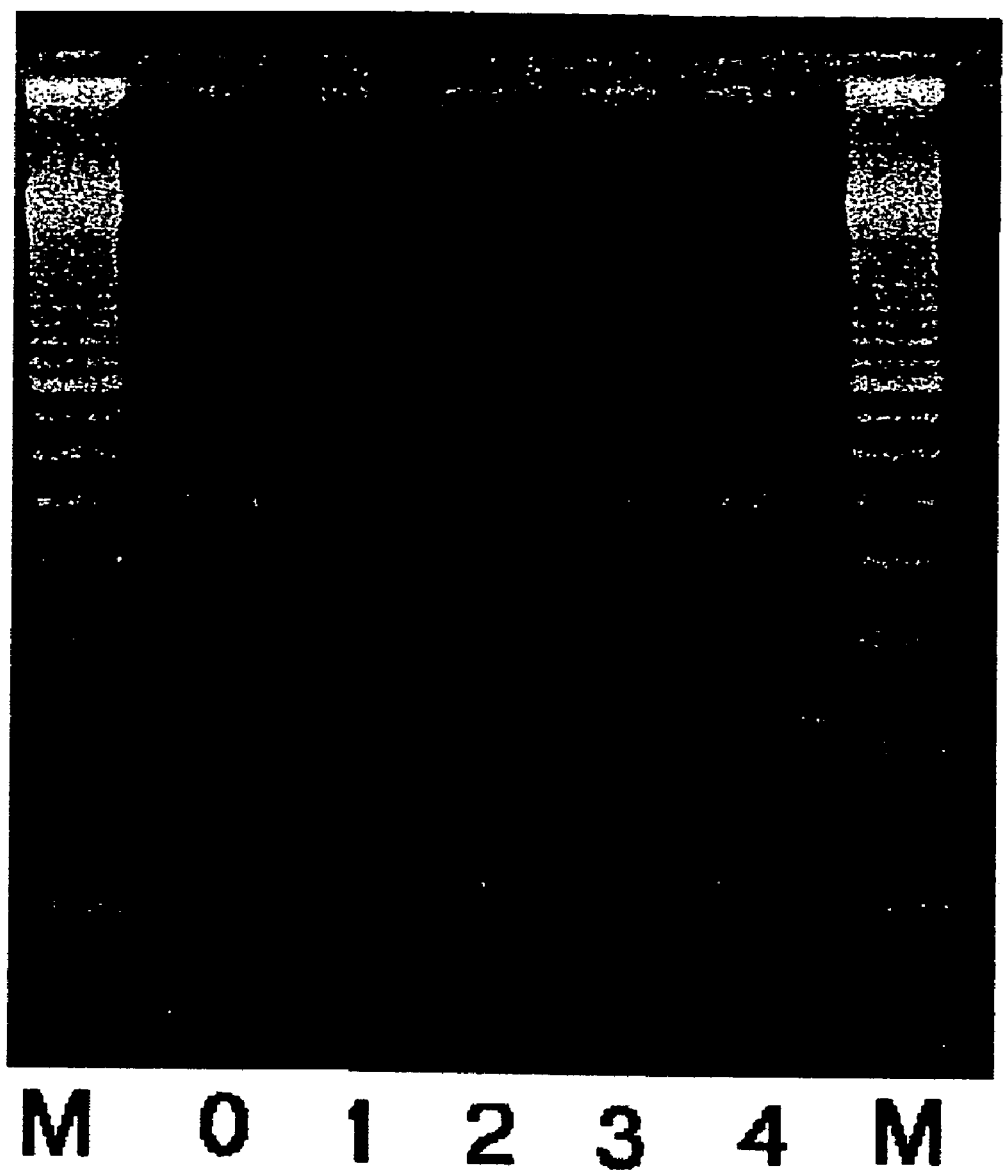
FIG. 1 is a migration picture, showing the confirmation result of immobilization and re-immobilization.

The method of reusing a DNA-immobilization substrate of the invention comprises removing the immobilized DNA from a DNA-immobilization substrate having a DNA immobilized thereon through acid amido-bonding via an oligonucleotide to thereby refresh the substrate so that it can receive a new DNA to be immobilized thereon, and is characterized in that the acid amido-bonding between the substrate-DNA is hydrolyzed with an acid or alkali.

The DNA immobilization substrate which is to be processed in the reusing method of the invention has a DNA immobilized on the amino group-modified substrate surface via acid amido-bonding.

Preferably, the amino group-modified substrate is prepared by aminating the surface of a substrate of, for example, diamond, silicon, glass, or metals such as gold, silver, copper, aluminum, tungsten, molybdenum, or laminates of the metals with ceramics, or plastics such as polycarbonates, fluororesins.

Apart from the above, any other chemically-stable materials are usable for the substrate, for example, graphite and diamond-like carbon. Also usable are mixtures of plastics with the above-mentioned metals, ceramics, diamond, etc. Also preferred for use herein are silicon, glass, metals, graphite, plastics and others coated with diamond or diamond-like carbon.

Of those, diamond is preferred in view of its thermal conductivity. Diamond has good thermal conductivity and accepts rapid heating and cooling. Therefore, the period of heat cycle for heating and cooling the substrate for bonding a DNA thereto can be effectively shortened.

Concretely, the thermal conductivity of the substrate material may be at least 0.1 W/cm·K, preferably at least 0.5 W/cm·K, more preferably at least 1.0 W/cm·K.

For the material of the diamond substrate, usable are any of synthetic diamond, high-pressure molded diamond, natural diamond, etc. Their structures may have any form of single-crystal or polycrystal. From the viewpoint of productivity thereof, diamond that is produced through vapor-phase synthesis, for example, through microwave plasma-assisted CVD, is preferred.

The substrate may be formed in any known method. For example, the method includes microwave plasma-assisted CVD, ECRCVD, IPC, DC sputtering, ECR sputtering, ion plating, arc ion plating, EB vapor deposition, resistance heating vapor deposition, etc. Metal powder, ceramic powder or the like may be mixed with a resin binder, and may be shaped into substrates for use herein. Apart from it, the starting material of metal powder, ceramic powder or the like may be pressed into a green compact by the use of a pressing machine and it may be sintered at high temperatures.

Preferably, the surface of the substrate is intentionally roughened. The roughened surface is favorable for immobilizing a large quantity of DNA or the like, since its surface area increases. The shape of the substrate is not specifically defined, and may be tabular, yarn-like, spherical, polygonal, powdery, etc. In addition, the size of the substrate is not also specifically defined.

The diamond substrate for use in the invention may include a composite that comprises diamond and any other substance (for example, a two-phase composite of diamond or diamond-like carbon).

The amino group modification of the substrate surface may be attained, for example, by irradiating a solid substrate with UV rays in chlorine gas to chlorinate the substrate surface followed by further irradiating it with UV rays in ammonia gas to aminate it.

The amino group-modified substrate surface may be modified with a carboxylic acid by carboxylating it with a suitable acid chloride followed by dehydrating and condensing the terminal carboxyl group with carbodiimide or dicyclohexylcarbodiimide and N-hydroxysuccinimide.

One example of dehydrating condensation according to this method is described. A solid substrate of which the surface has been modified to have a carboxyl group is dipped in a 1,4-dioxane solution with carbodiimide or dicyclohexylcarbodiimide, and N-hydroxysuccinimide or p-nitrophenol dissolved therein, then washed and dried. Thus processed, the substrate has a hydrocarbon group with an N-succinimide ester group or p-nitrophenol ester bonded to the terminal thereof.

More preferably in the above-mentioned method, a primary amino group is previously formed on the diamond substrate, and this is processed with an activated diester so as to have one ester group of the diester bonded to the primary amino group through dehydrating condensation.

The activated diester has two active ester groups such as those mentioned hereinabove. Preferably, the ester groups are positioned at both terminals of the activated diester, and have from 0 to 12, more preferably from 0 to 6 carbon atoms each. Also preferably, the skeleton moiety except the ester groups is a linear saturated fatty acid.

In the method of using such an activated diester, a substrate may be chlorinated in the same manner as above and then aminated, and thereafter the amino group in this may be reacted with an activated ester that is previously prepared through activating esterification of N-hydroxysuccinimide with succinic acid (dicarboxylic acid) to obtain the intended substrate.

The substrate thus having a carboxylic acid-modified surface and having a DNA immobilized on the surface via an oligonucleotide is to be processed according to the invention for reusing it.

The DNA to be immobilized on the substrate is not specifically defined, and may be any of a single-stranded cDNA (complementary DNA) or a double-stranded cDNA (genomic DNA, chromosomal DNA). The chain length of the DNA is not also specifically defined.

The oligonucleotide shall be suitably selected, depending on the type of the DNA to be bonded to the substrate. In case where a single-stranded cDNA is immobilized on the substrate, it may take advantage of reverse transcription with mRNA for a template, and an oligo-dT or the like that may be a primer for the reverse transcription may be used for the oligonucleotide.

On the other hand, immobilization of a double-stranded gDNA may be effected by the use of restriction enzyme cleavage sites. In this case, the oligonucleotide to be used shall have a restriction enzyme cleavage site on the DNA bonding side.

In the invention, used DNA-immobilization substrates that are useless are dipped in an acid or alkali solution whereby the acid amido-bonding between the substrate-DNA is hydrolyzed and cleaved, and the surfaces are thereby refreshed to have an amino group-modified surface.

The acid to be used for the hydrolysis is preferably a mineral acid such as hydrochloric acid, but may be any other mineral acid or organic acid capable of hydrolyzing acid amido-bonding.

In case where an alkali is used for the hydrolysis, it is preferably an alkali metal hydroxide, but may be any other alkaline salts such as alkali metal carbonates.

The condition for the hydrolysis is described. For acid hydrolysis, a DNA-immobilized substrate is put into 6 M hydrochloric acid and reacted at 80 to 100° C. for a few hours to 24 hours to thereby completely hydrolyze the acid amido-bonding between the substrate-DNA.

For alkali hydrolysis, a DNA-immobilized substrate is put into 2 M NaOH and reacted at room temperature for a few hours to 24 hours to thereby hydrolyze the acid amido-bonding between the substrate-DNA.

After the acid hydrolysis, the substrate surface has anions thereon. Preferably, therefore, it is dipped in an alkali to remove the anions and then washed with water.

On the other hand, the alkali-hydrolyzed substrate may be washed with water, not requiring any additional treatment.

Accordingly, the acid amido-bonding between the substrate-DNA in the DNA-immobilized substrate is hydrolyzed, and the amino group-modified surface of the substrate is thereby exposed out.

After thus processed, the substrate may be reused for carboxylic acid modification, oligonucleotide immobilization and DNA immobilization in the manner as above.

EXAMPLES

The invention is described in detail with reference to the following Examples.

Example 1

A diamond substrate was used. The substrate mentioned below is the diamond substrate.

The substrate with a DNA immobilized thereon was put into 6 N hydrochloric acid and reacted at 95° C. for 5 hours to hydrolyze it. Then, this was washed (about 3 times). In this condition, the substrate had a hydrochloride. Therefore, this was dipped in a 0.1 N potassium hydroxide solution to remove the chloride ions from it. With that, the substrate was washed with water (about 3 to 5 times) to thereby make it have an amino group-modified surface.

0.1 mmols of succinic acid chloride was added to 1 ml of chloroform, and the reusable amino group-modified substrate was inserted into it and reacted at room temperature for 30 minutes. Next, the substrate was washed with chloroform, dried, then dipped in pure water for 1 hour, and then finally washed with pure water (about 3 to 5 times) to make it have a succinic acid-modified surface.

0.1 mmols of water-soluble carbodiimide and 0.1 mmols of hydroxysuccinimide were dissolved in 1 ml of 90% 1,4-dioxane, and the succinic acid-modified substrate was dipped in it and reacted at a high temperature for 15 minutes with shaking. The substrate was taken out and washed with 1,4-dioxane (about 2 to 4 times) and with pure water (about 3 to 5 times).

The substrate was dipped in an aqueous solution of an oligonucleotide having a restriction enzyme (EcoRI) site and having (dA)$_3$ at the 5' terminal (concentration: 500 fmol/μl, 50 μl per one substrate), and reacted at room temperature for 1 hour.

Then, this was dipped in an aqueous solution of an oligonucleotide having a complementary sequence to the immobilized oligonucleotide (concentration=500 fmol/μl, 50 μl per one substrate) at 4° C. for 30 minutes for hybridization.

The substrate was dipped in an EcoRI reaction liquid and reacted at 37° C. for 1 hour. Then, the reaction mixture was cooled to 4° C., and the substrate was taken out of it. This was washed with germ-free water cooled at 4° C. (about 3 to 5 times) and then with an aqueous 60% ethanol solution cooled at 4° C., and thereafter lightly dried (for ethanol evaporation).

The substrate was dipped in a ligase solution that contained a 21-kbp fragment obtained by processing λDNA with EcoRI, and reacted overnight at 4° C. to thereby immobilize the DNA on the substrate.

The hydrolysis and the DNA re-immobilization on the substrate was confirmed as follows: The substrate was subjected to PCR with a primer capable of amplifying the 500-bp fragment in the 21-kbp μDNA fragment, and checked for DNA amplification thereon. FIG. 1 shows the result.

FIG. 1 is a migration picture, showing the confirmation result of immobilization and re-immobilization. In FIG. 1, the mark M described under the migration picture indicates a 100-bp lag marker; the lane 0 indicates the substrate before hydrolysis; the lanes 1 and 2 indicate the substrates after hydrolysis; and the lanes 3 and 4 indicate the substrates after re-immobilization.

As in FIG. 1, it was confirmed that the DNA having been immobilized on the substrate was removed from the hydrolyzed substrate, and a new DNA was re-immobilized on the substrate.

INDUSTRIAL APPLICABILITY

According to the reusing method of the invention, the DNA can be completely removed from DNA-immobilized substrates that are useless, and a new DNA can be bonded to the thus-refreshed substrates.

In addition, since the reusing method of the invention does not require any specific reagent and apparatus, it is simple and inexpensive.

Further, since expensive DNA-immobilization substrate can be reused according to the invention, the invention promotes economical diagnoses and studies that use DNA-immobilization substrates for gene diagnosis, etc.

Accordingly, the reusing method of the invention is useful in the field of medicine and other various fields of molecular biology, biochemistry and gene engineering technology.

The invention claimed is:

1. A method of reusing a DNA-immobilization substrate, which consists of removing the immobilized DNA from a DNA-immobilization substrate having a DNA immobilized thereon through acid amido-bonding via an oligonucleotide to thereby refresh the substrate so that it can receive a new DNA to be immobilized thereon, and which is characterized in that the acid amido-bonding between the substrate-DNA is hydrolyzed with hydrochloric acid.

2. A method of reusing a DNA-immobilization substrate, which comprises treating a DNA-immobilization substrate with a DNA that has been immobilized thereon by an acid amido-bonding to thereby hydrolyze the acid amido-bonding between the substrate-DNA by dipping the substrate into an hydrochloric acid, and then dipping the substrate into an alkali to remove anions so as to convert the substrate surface into an amino group-modified surface.

* * * * *